United States Patent
Dai et al.

(10) Patent No.: US 12,044,655 B2
(45) Date of Patent: Jul. 23, 2024

(54) DOWNHOLE WELL PIPE INSPECTION USING OPTIMIZED INSPECTION TOOLS

(71) Applicant: Halliburton Energy Services, Inc., Houston, TX (US)

(72) Inventors: Junwen Dai, Houston, TX (US); Ahmed Fouda, Houston, TX (US)

(73) Assignee: Halliburton Energy Services, Inc., Houston, TX (US)

(*) Notice: Subject to any disclaimer, the term of this patent is extended or adjusted under 35 U.S.C. 154(b) by 422 days.

(21) Appl. No.: 17/539,272

(22) Filed: Dec. 1, 2021

(65) Prior Publication Data
US 2023/0168226 A1 Jun. 1, 2023

(51) Int. Cl.
G01N 27/9093 (2021.01)
G01N 33/2045 (2019.01)
G06F 30/18 (2020.01)
G06F 113/14 (2020.01)

(52) U.S. Cl.
CPC ..... *G01N 27/9093* (2013.01); *G01N 33/2045* (2019.01); *G06F 30/18* (2020.01); *G06F 2113/14* (2020.01)

(58) Field of Classification Search
CPC . G01N 27/9093; G01N 33/2045; G01N 27/82
See application file for complete search history.

(56) References Cited

U.S. PATENT DOCUMENTS

| | | |
|---|---|---|
| 7,960,969 B2 | 6/2011 | Mouget et al. |
| 9,715,034 B2 | 7/2017 | Omeragic et al. |
| 9,983,173 B2 | 5/2018 | Aslanyan et al. |
| 10,502,044 B2 | 12/2019 | Fouda et al. |
| 2015/0015265 A1 | 1/2015 | Seydoux et al. |

(Continued)

FOREIGN PATENT DOCUMENTS

| | | |
|---|---|---|
| EP | 0873465 B1 | 3/2002 |
| WO | WO 2018/031047 A1 | 2/2018 |
| WO | WO 2018/222209 A1 | 12/2018 |

OTHER PUBLICATIONS

Search Report and Written Opinion issued for International Patent Application No. PCT/US2021/060009, dated Aug. 11, 2022, 10 pages.
Search Report and Written Opinion issued for International Patent Application No. PCT/US2021/061324, dated Aug. 17, 2022, 11 pages.

(Continued)

*Primary Examiner* — Lisa M Caputo
*Assistant Examiner* — Cynthia L Davis
(74) *Attorney, Agent, or Firm* — John W. Wustenberg; C. Tumey Law Group PLLC

(57) ABSTRACT

Electromagnetic logging tools are optimized using synthetic logs for the purpose of pre-job planning and accuracy/resolution estimation. One, two and three-dimensional forward modeling are used to generate accurate inspection tool responses. A radial one-dimensional (R1D) electromagnetic forward model is also used to compute an approximate log. By constructing non-linear mapping functions between the R1D model-based log and the 2D model-based log, and mapping the R1D synthetic log using the non-linear mapping functions, a quasi 2D log is computed. The quasi 2D log is processed using model-based inversion, thereby providing estimates of pipe parameters. By analyzing the estimates of pipe parameters, tool performance metrics are obtained and analyze to determine the performance of the tool. The tool parameters are adjusted in order to optimize the performance metrics.

20 Claims, 12 Drawing Sheets

(56) References Cited

U.S. PATENT DOCUMENTS

| | | |
|---|---|---|
| 2015/0127274 A1 | 5/2015 | Legendre et al. |
| 2017/0114628 A1 | 4/2017 | Khalaj Amineh et al. |
| 2018/0106763 A1 | 4/2018 | Fouda et al. |
| 2018/0106764 A1 | 4/2018 | Fouda et al. |
| 2019/0040734 A1 | 2/2019 | Burkay et al. |
| 2019/0086320 A1 | 3/2019 | Guner et al. |
| 2019/0162870 A1 | 5/2019 | San Martin et al. |
| 2019/0369285 A1 | 12/2019 | Fouda et al. |
| 2020/0081148 A1 | 3/2020 | Capoglu et al. |
| 2020/0200940 A1 | 6/2020 | Fouda et al. |
| 2020/0333500 A1 | 10/2020 | Fouda et al. |
| 2021/0239874 A1 | 8/2021 | Fouda |
| 2021/0349231 A1 | 11/2021 | Griffing et al. |

OTHER PUBLICATIONS

Search Report and Written Opinion issued for International Patent Application No. PCT/US2021/061327, dated Aug. 24, 2022, 12 pages.

Garcia et al., "Successful Application of a New Electromagnetic corrosion Tool for Well Integrity Evaluation in Old Wells Completed with Reduced Diameter Tubular," International Petroleum Technology Conference, Beijing, China, Mar. 26-28, 2013.

Haugland, "Fundamental Analysis of the Remote-Field Eddy-Current Effect," IEEE Transactions on Magnetics, vol. 32, No. 4, Jul. 1996, pp. 3195-3211.

Yu, et al., "An Advanced Technique for Simultaneous in Situ Inspection of Multiple Metallic Tubulars," SPE/ICoTA Well Intervention Conference and Exhibition, The Woodlands, Texas, USA, Mar. 2019.

DOWNHOLE WELL PIPE INSPECTION USING OPTIMIZED INSPECTION TOOLS

FIELD OF THE INVENTION

The present invention relates generally to hydrocarbon exploration using electromagnetic logging and, more specifically, to methods and systems to inspect nested downhole pipes using inspection tools having parameters which have been adjusted to optimize performance metrics.

BACKGROUND

Electromagnetic ("EM") techniques are commonly used to monitor the condition of pipes in oil and gas wellbores, including various kinds of casing strings and tubing. One common EM technique is the eddy current technique. In the eddy current technique, when the transmitter coil emits the primary transient EM fields, eddy currents are induced in the casing. These eddy currents then produce secondary fields which are received along with the primary fields by the receiver coil. The acquired data can be then employed to perform evaluation of the multiple pipes.

A typical wellbore diagram comprises multiple nested pipes. The number of casing layers used depends on the characteristics of the subsurface and can vary from well to well. Depending on a well's design, well construction can have between two and four main components. These components include conductor, surface, intermediate and production casings. After completion of the well, a tubing may be inserted to pump hydrocarbon products. When the EM tool is used to monitor the pipe condition, the log is affected by many factors including, for example, the pipe electrical properties and pipe geometry including number, size, and shape. The number of casings is one of the influential factors which significantly impacts the signal level.

The well diagram (design of the well) varies from well to well. Even for wells which theoretically are the same, the pipe configuration still changes. Therefore, each well requires an inspection tool having a different number of sensors and different logging speeds. For example, for a well diagram having a section with five pipes, it requires more receivers to see all pipes in one single run. It also needs a longer time to establish a steady response to maintain the high signal-to-noise ratio. Inappropriate logging speeds have resulted in logs with deteriorated quality. Thus, it is important to configure the tool and estimate the logging speed before logging to obtain optimal data quality for each job.

Furthermore, besides the tool specifications, for example, sensitivity, accuracy, and vertical resolution also depend on the well diagram. A general estimation of these metrics is inaccurate for any given specific well. Thus, existing approaches sometimes provide inaccurate tool specifications for customers.

DESCRIPTION OF ILLUSTRATIVE EMBODIMENTS

Figure 1:
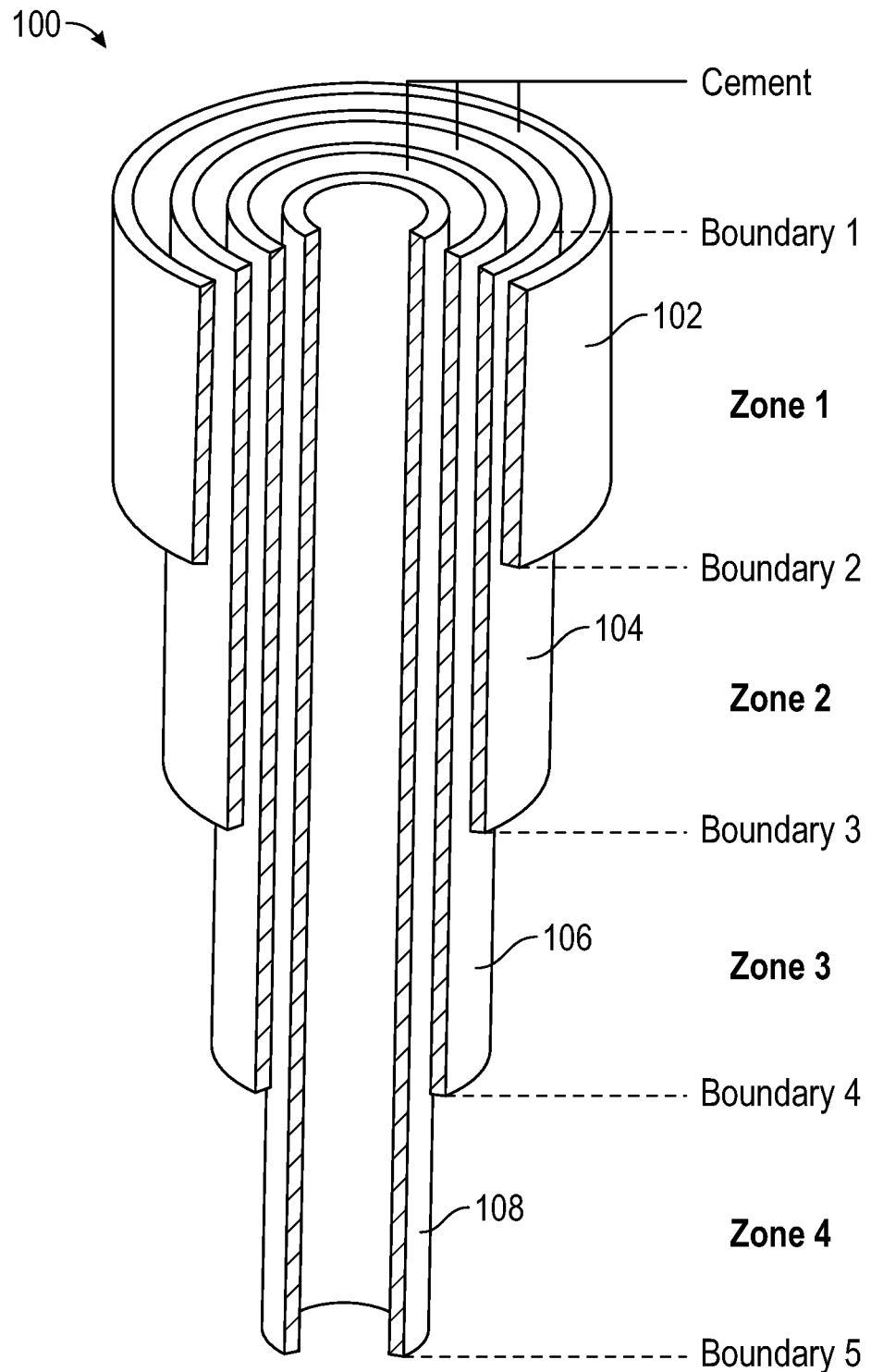
FIG. 1 is a well casing diagram useful to illustrate principles of the present disclosure.

Illustrative embodiments and related methods of the present disclosure are described below as they might be employed to inspect nested tubulars using an inspection tool which has been optimized using the modeling techniques described herein. In the interest of clarity, not all features of an actual implementation or methodology are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. Further aspects and advantages of the various embodiments and related methodologies of the invention will become apparent from consideration of the following description and drawings.

Exemplary embodiments of the present invention are directed to systems and methods to inspect wellbore pipes using inspection tools optimized through use of the modeling techniques described herein. The present disclosure provides methods to efficiently generate synthetic logs for the purpose of pre-job planning and accuracy/resolution estimation. A two-dimensional (2D) electromagnetic forward modeling is used to generate accurate inspection tool responses. A radial one-dimensional (R1D) electromagnetic forward model is also used to efficiently compute an approximate log. By constructing non-linear mapping functions between the R1D model-based log and the 2D model-based log, and mapping the R1D synthetic log using the non-linear mapping functions, a quasi 2D log is computed. The quasi 2D log is then processed using model-based inversion, thereby providing estimates of pipe parameters. By analyzing the estimates of pipe parameters, tool performance metrics are obtained (e.g., accuracy, vertical resolution) and analyze to determine the performance of the tool. Therefore, the tool parameters are adjusted in order to optimize the performance metrics.

In addition, this disclosure also provides methods to customize the electromagnetic tool parameters based on the well diagram. For example, an array of transmitters and/or receivers is selected before running the tool based in part upon the well diagram. Also, the decisions to excite certain transmitters and acquire from certain receivers is determined prior to running the tool based in part on the well plan.

In a generalized method of the present disclosure, well plan/diagram information is first obtained. Based upon the well plan information, a pipe inspection tool is modeled in a pipe inspection scenario to thereby obtain synthetic data. The synthetic data is analyzed to obtain performance metrics of the pipe inspection tool using a set of tool parameters. The tool parameters are then adjusted to optimize the performance metrics of the pipe inspection tool. A real-world, physical pipe inspection tool having the adjusted tool parameters is then positioned along a well and used to acquire measured data. The measured data is then used to determine well pipe parameters.

FIG. 1 is a well casing diagram. As can be seen, the well casing 100 consists of four pipes with different lengths and four zones with a different number of concentric pipes. The number of casing layers used depends on the characteristics of the subsurface and can vary from well to well. In this example, the components include a conductor casing 102, surface casing 104, intermediate casing 106 and production casings 108. Each casing string defines a zone 1, zone 2, zone 3 and zone 4. When the EM inspection tool is used to monitor the pipe condition, the log is affected by many factors, for instance, the pipe electrical properties and pipe geometry including number, size, and shape.

As one kind of electromagnetic (EM) technique, the eddy current (EC) effect of EM waves can be applied to develop a tool to characterize the pipe around the borehole. In frequency-domain EC techniques, a transmitter coil is fed by a continuous sinusoidal signal, producing primary fields that illuminate the pipes. The primary fields produce eddy currents in the pipes. These eddy currents, in turn, produce secondary fields that are sensed along with the primary fields in the receiver coils that are placed at a distance from the transmitter. Characterization of the pipes is performed by measuring and processing these fields.

In frequency-domain EC techniques, a transmitter coil is fed by a continuous sinusoidal signal, producing primary fields that illuminate the pipes. The primary fields produce eddy currents in the pipes. These eddy currents, in turn, produce secondary fields that are sensed along with the primary fields in the receiver coils that are placed at a distance from the transmitter. High-frequency/short-spacing receivers are employed for inner pipes inspection. Low-frequency/long-spacing receivers are employed for outer pipes inspection.

In time-domain EC techniques (also referred to as pulsed EC (PEC)), the transmitter is fed by a pulse. Similar to the frequency-domain technique, transient primary fields are produced due to the transition of the pulse from "off" to "on" state or from "on" to "off" state. These transient fields produce eddy currents in the pipes. The eddy currents then produce secondary magnetic fields that are measured by either a separate receiver coil placed further away from the transmitter, a separate coil co-located with the transmitter, or the same coil that was used as the transmitter. Decay response is measured with the receiver coil. The response consists of wideband data.

Still referencing FIG. 1, Frequency-domain inspection tools provide high vertical resolution for inner pipes (e.g., intermediate casing 106 and production casing 108), but suffer degraded vertical resolution for outer pipes (e.g., conductor casing 102 and surface casing 104) because of the need to use longer transmitter-receiver spacing to penetrate deeper into the pipes. Time-domain tools on the other hand, require impractically high dynamic range and sampling rate to sample both the leading portion of the decay response that is sensitive to inner pipes (e.g., intermediate casing 106 and production casing 108), in addition to the trailing portion that is sensitive to both inner and outer pipes.

Figure 2B:
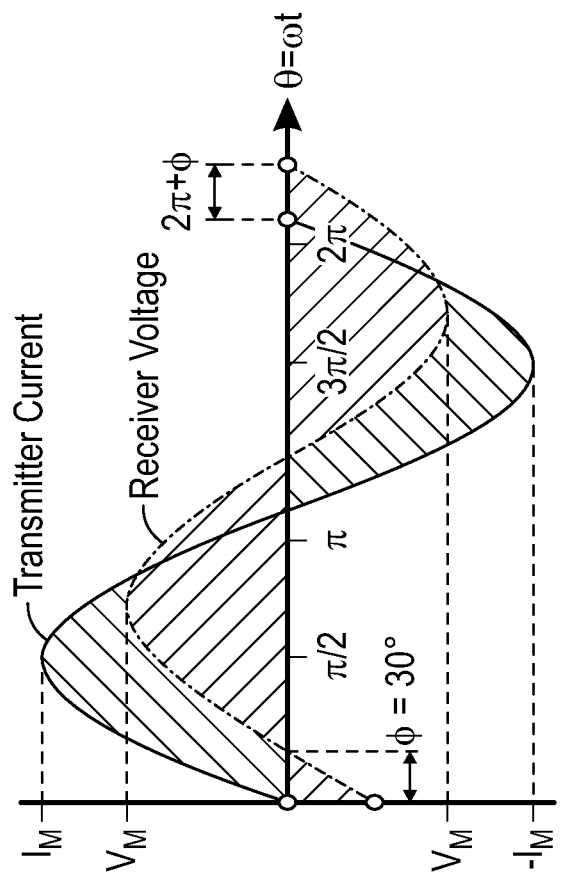
FIG. 2B is a graph showing continuous transmitter and receiver wave responses in the frequency domain.
Figure 2A:
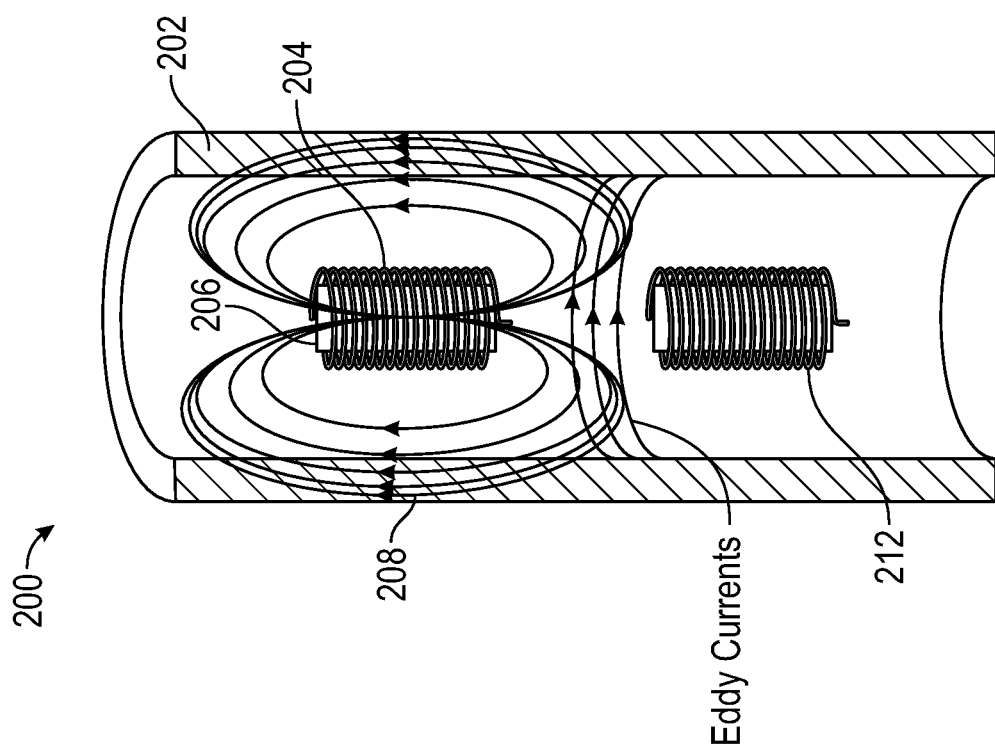
FIG. 2A is a view of a frequency-domain tool positioned inside a downhole pipe.

FIGS. 2A-2B are useful to further describe the advantages of the present disclosure. FIG. 2A is a view of a frequency-domain tool positioned inside a downhole pipe. Such tools typically have the following adjustable tool parameters: transmitter-receiver spacing, transmitter/receiver lengths, excitation current power, excitation current frequency, and logging speed. FIG. 2B is a graph showing continuous transmitter and receiver wave responses in the frequency domain. The eddy current effect on the EM wave can be applied to develop a tool to characterize the pipe around the borehole. As shown in FIG. 2A, inspection tool 200 is positioned inside a downhole tubular 202. In certain frequency-domain eddy current techniques, transmitter coil 204 (surrounding magnetic core 206) is fed by a continuous sinusoidal signal, producing primary fields 208 that illuminate the pipe(s) 202.

The primary fields produce eddy currents in pipes 202. These eddy currents, in turn, produce secondary fields that are sensed along with primary fields 208 in receiver coils 212 (also surrounding a magnetic core) that are placed at a distance from transmitter 204. High-frequency/short-spacing receivers are employed for inner pipe inspection. In certain examples, frequency domain responses may be acquired using short spacing receivers such as, for example, receivers which are spaced apart by less than 3 feet. The short spacing receivers are designed such that a change in the thickness of an inner pipe causes a substantially larger change in the receiver signal as compared to the receiver signal change caused by a similar change in an outer pipe thickness (thus making the short spacing receiver more sensitive to inner pipes). Here, the "substantially larger" change in the receiver signal may be, for example, a signal change of 5 to 15 percent. A "similar" change in pipe thickness, for example, would be a change in the range of 10 percent. In like manner, low-frequency/long-spacing receivers are employed for outer pipe inspection because they are designed such that a change in the thickness of the outer pipe causes a substantially larger change in the receiver signal as compared to the receiver signal change cause by a similar thickness change in an inner pipe, thus making it more sensitive to outer pipes. Long spacing receivers may be, for example, receivers which are spaced apart by 3 to 10 feet. Characterization of the pipes is performed by measuring and processing these fields.

Figure 3B:
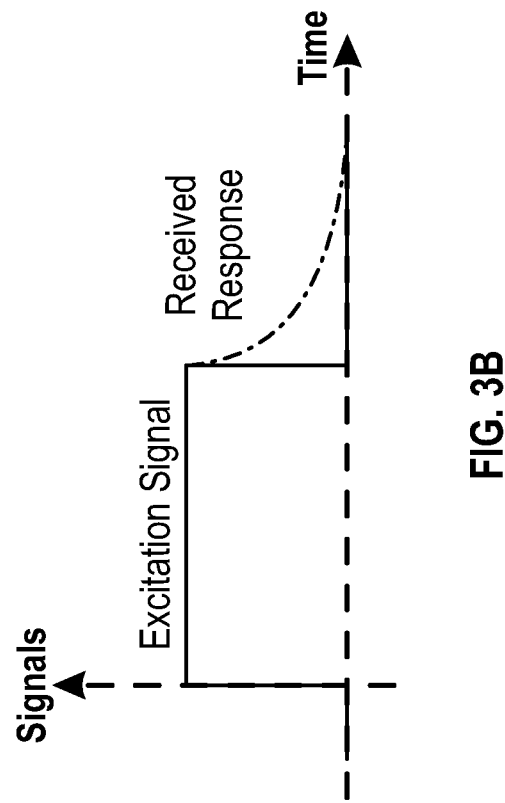
FIGS. 3A and 3B illustrate a time-domain inspection tool and its associated response, respectively.
Figure 3A:
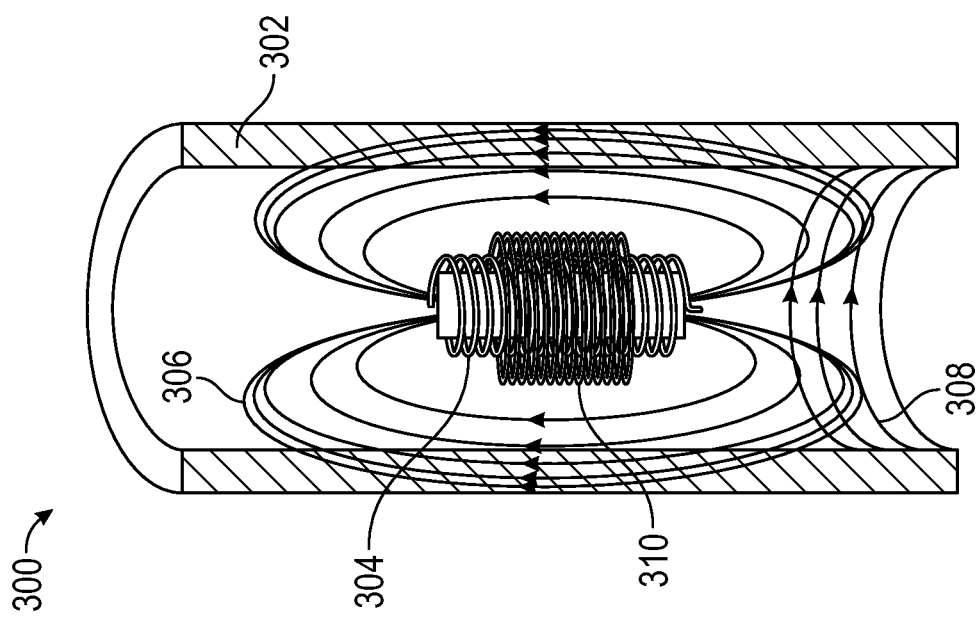

FIGS. 3A and 3B illustrates a time-domain inspection tool and its associated response, respectively. In this case, the adjustable tool parameters include transmitter/receiver lengths, excitation current power, excitation pulse duration, excitation pule slew rate, decay response recording time duration, decay response sampling rate, and logging speed. In this example, a time domain inspection tool 300 is positioned inside a downhole pipe 302. In time-domain eddy current techniques (also referred to as pulsed eddy current or PEC), transmitter 304 is fed by a pulse. Similar to the frequency-domain technique, transient primary fields 306 are produced due to the transition of the pulse from "off" to "on" state or from "on" to "off" state. These transient fields 306 produce eddy currents 308 in the pipes 302. The eddy currents 308 then produce secondary magnetic fields (not shown) that are measured by either a separate receiver coil placed further away from transmitter 304 (not shown), a separate receiver coil 310 co-located with transmitter 304, or the same coil that was used as the transmitter (not shown). As shown in FIG. 3B, the decay response (received response) is measured with the receiver coil 310. The response consists of wideband data.

Figure 4:
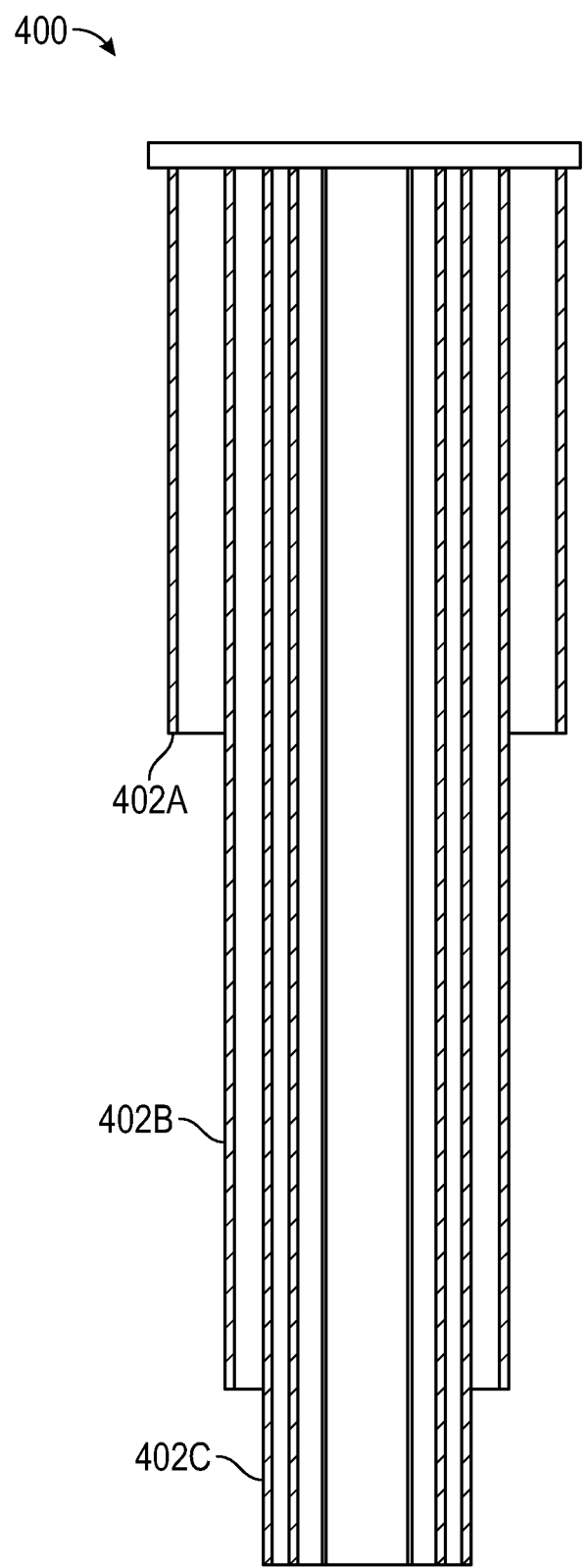
FIG. 4 is a section view of a well diagram/plan, according to an illustrative embodiment of the present disclosure.

FIG. 4 is a section view of a well diagram/plan, according to an illustrative embodiment of the present disclosure. Well plan 400 includes casing pipes 401A, 402B and 402C. Well plan 400 comprises information on at least one of the nominal outer diameter of the pipes 402A, B or C, the nominal thickness of the pipes 402A, B or C, the start and end depths of the pipes 402A, B or C, the grade and weight of the pipes 402A, B or C, the type of metal of the pipes 402A, B or C (e.g. carbon steel vs. alloyed).

Because of the complexity of the well diagram, the inspection tool should be configurable to obtain the optimal performance. In certain illustrative embodiments, the well diagram can be obtained from the customer when the well is completed. The well diagram comprises information, for example, on the starting and ending depths of the pipes, the nominal outer diameters of the pipes, the type of metal of the pipes (e.g., carbon steel vs. alloyed), and the nominal thickness of the pipes or the grade and weight of the pipes.

According to certain illustrative embodiments of the present disclosure, based on the well diagram, the system can adjust the tool configuration to optimize performance of the tool. For example, various tool components and characteristics can be adjusted including the number of transmitters and receivers, transmitter-receiver spacing, transmitter/receiver lengths, excitation current power, excitation current frequency, excitation pulse duration, excitation pule slew rate, decay response recording time duration, decay response sampling rate, and logging speed. For example, the travel time for the electromagnetic wave to propagate from the transmitter in the borehole to reach the outmost pipe and reflect back to the receiver in the borehole can be calculated using the following equation:

$$t = \frac{2d}{c}\sqrt{\frac{\sigma\mu_r}{j2\pi f \varepsilon_0}},\qquad \text{Eq. 1}$$

where d is the total thickness of all pipes, c and $\varepsilon_0$ are the light speed and permittivity in the vacuum, $\sigma$ and $\mu_r$ are the electrical conductivity and magnetic permeability of pipes, f is the operating frequency of the tool. Based upon these variables (which will be known based on the well plan), the wave travel time will be determined. Once the travel time is known of the various low or higher frequency waves which can be used, the most optimal inspection tool characteristics (e.g., number of transmitters/receivers the transmitter-receiver spacing, excitation current power, logging speed, etc.) can be determined.

The travelling speed of low frequency waves interacting with the metallic pipe is slower than higher frequency wave. Furthermore, the low frequency wave is designed for inspecting the outer pipe, because it can penetrate more pipes. The travelling distance is longer for low frequency wave. Thus, it can be concluded that it will take longer time to establish a steady response when low frequency waves are used. Therefore, in this example, the configuration of the frequency domain tool is determined based upon the well plan. Further, the decision to excite certain transmitters and acquire from certain receivers is determined prior to running the tool based in part on the well plan.

Figure 5:
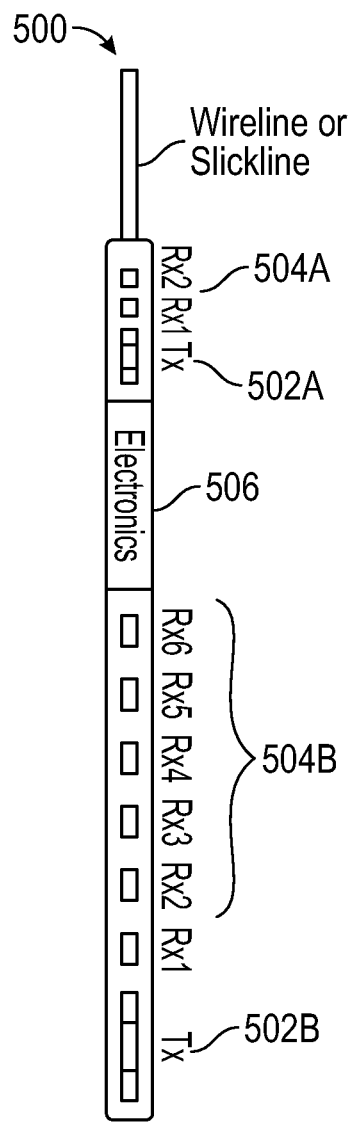
FIG. 5 is a perspective view of an illustrative frequency domain tool constructed according to certain illustrative embodiments of the present disclosure.

FIG. 5 is a perspective view of illustrative frequency domain tools constructed according to certain illustrative embodiments of the present disclosure. In FIG. 5, the frequency domain inspection tool 500 is a tool which has previously been assembled. Tool 500 includes an array of transmitters 502a and 502b and receivers 504a and 504b, along with control system electronics 506. In this example, the decision on which receivers and transmitters to excite and acquire from are determined prior to running the tool, based on the well plan analysis and simulation described herein.

Once the tool configuration is determined (e.g., for tool 500), the excitation current strength, operation frequency, and logging speed can be dynamically adjusted by the system based on the surrounding pipe configurations, as discussed above. For example, in the well area with more pipes, the low-frequency channels should be activated, and larger excitation current strength should be applied, and logging speed should be tuned to a low speed. In this way, the field engineer can obtain high quality log data with high signal-to-noise and saving operation time and power consumption. Although not shown in FIG. 5, in certain examples, inspection tools 500 is communicably coupled to a control system to control the dynamic adjustment of these operational characteristics.

Figure 6:
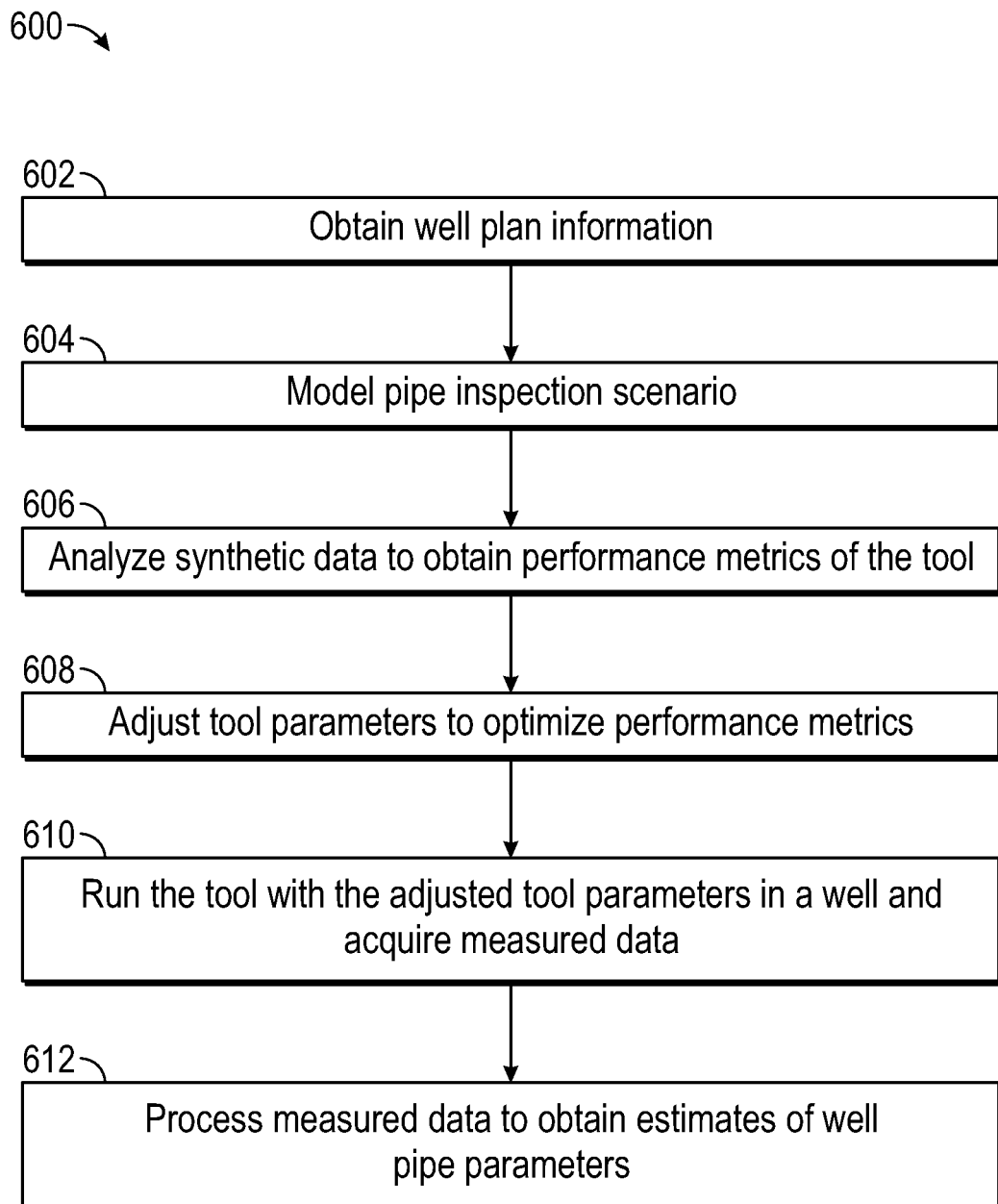
FIG. 6 is a method to inspect nested pipes, according to certain illustrative methods of the present disclosure.

In view of the foregoing, FIG. 6 is a flow chart of a method to inspect a wellbore pipes, according to certain illustrative methods of the present disclosure. In method 600, at block 602 the computer/control system obtains the well diagram information. At block 604, the computer system models a pipe inspection scenario using a computer model constructed based upon the well plan to obtain synthetic data. In certain illustrative methods, the computer model is a radial 1-dimensional electromagnetics model, a 2-dimensional model or a 3-dimensional model. The modeled scenario comprises, in this example, the nominal pipe parameters from the well diagram with at least one defect on at least one pipe. The synthetic data is generated by the computer system running the computer model for the given well plan with defect profiles of interests.

At block 606, the system analyzes the synthetic data to obtain performance metrics of the tool with a given set of tool parameters/characteristics in the given scenario. Here, the synthetic data is process using inversion to obtain estimates of the modeled pipe parameters. The system then analyzes the performance metrics of the modeled tool which can include, for example, the tool's inversion accuracy/sensitivity in resolving individual pipe thicknesses, the inversion stability with respect to the model vs. inversion mismatch, the tool sensitivity, signa-to-noise ratio, vertical resolution of the tool, variations in pipe material properties, physical tool structure, or random noise.

To further describe block 606, inversion is a type of data processing to convert the measurements into the quantity of interest, for example individual pipe thicknesses in one example. Thus, the accuracy of the inversion result is an important metric to evaluate tool performance. The pipe thickness may be measured from one direction, i.e., the radial direction to evaluate tool performance. The vertical resolution is another direction, which is along the tool direction. Only when the defect (metal loss due to corrosion) is longer than the vertical resolution can the tool accurately estimate the pipe thickness. The smaller the vertical resolution is, the better the tool is. Inversion stability is a metric to evaluate inversion solver performance since the inversion can be affected by some factors (e.g., eccentricity, pipe material properties, random noise.). If inversion solver is stable and less affected by these factors, that means the inversion solver can provide an accurate solution of pipe thickness.

Once the tool's performance metrics are determined, at block 608, the system can adjust the tool parameters in order to optimize the performance metrics based on the estimates of the modeled pipe parameters. This process may be performed iteratively until the optimal performance metrics are determined. At block 610, a real world tool having the adjusted (optimized) tool parameters is then run into a well and acquires measured data. At block 612, that data is then processed to obtain estimates of the well pipe parameters using a model based inversion. Further, as the tool is being operated in real-time, the tool parameters may be updated based upon changes in the well environment.

Figure 7:
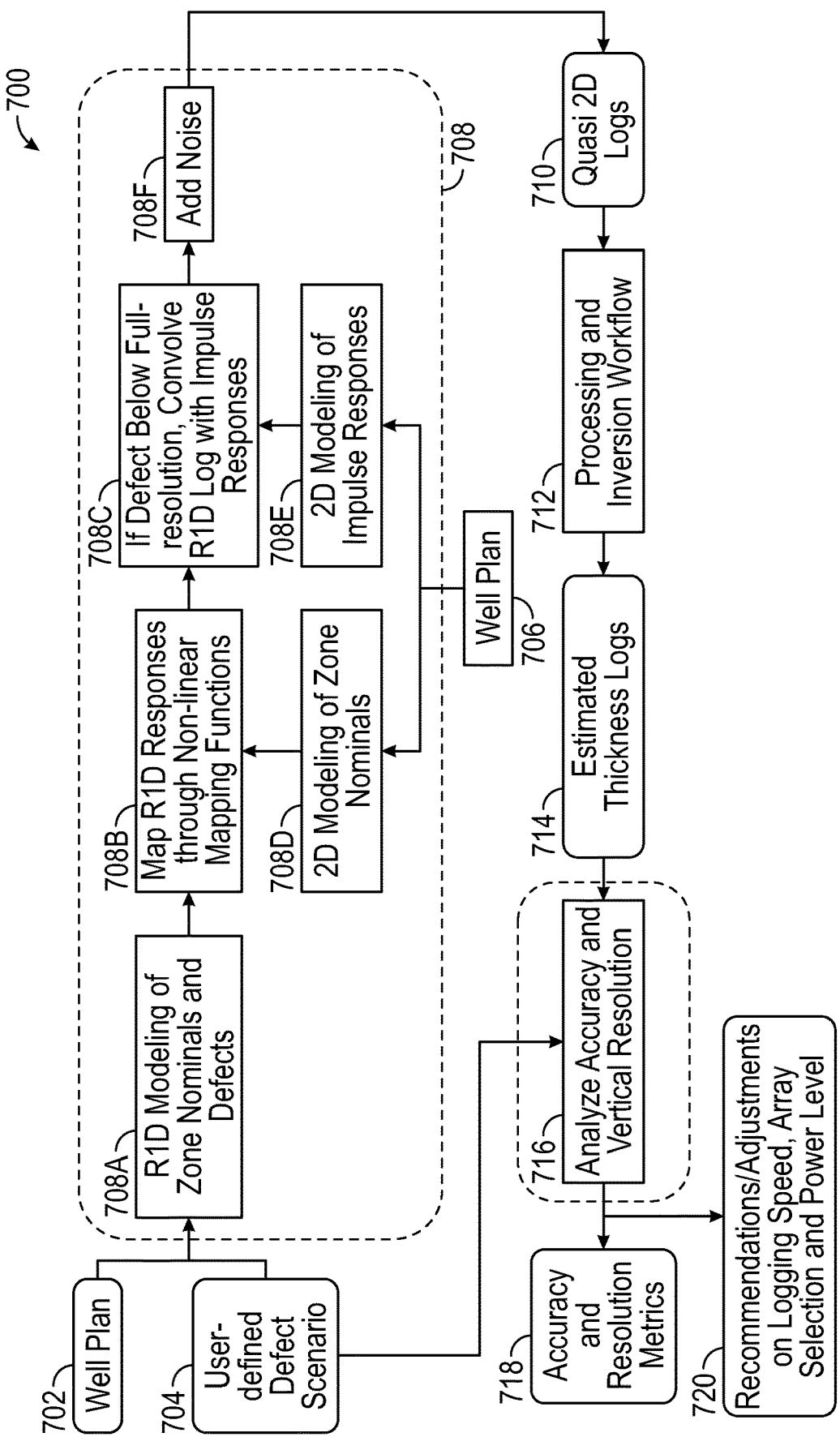
FIG. 7 is a workflow diagram of an illustrative method to plan the electromagnetic pipe inspection jobs.

In other illustrative methods of the present disclosure, the system also determines a plan for the electromagnetic pipe inspection jobs. FIG. 7 is a workflow diagram of an illustrative method to plan the electromagnetic pipe inspection jobs. Workflow 700 begins again with obtaining well plan information at blocks 702 and 704, along with a user-defined pipe defect scenario to be simulated at block 706. In block 708, using the well plan and defect input data, the system generates the synthetic data. As shown in FIG. 4, from the well diagram, there are five casings deployed at different depths. From top to bottom, this well can be divided into three zones (zone 1, 2, and 3) by four boundaries. In this example, each pipe zone has the same pipe configuration, like pipe number and pipe size. For each pipe zone, the system models a pipe scenario with the zonal nominal parameters (described below) using a radial 1-dimensional (R1D) computer model to obtain synthetic data log at block 708A.

A typical wellbore diagram comprises multiple nested pipes. Depending on a well's design, well construction can have between two and four main components. These components include conductor, surface, intermediate and production casings. After completion of the well, a tubing may be inserted to pump hydrocarbon products. When the EM tool is used to monitor the pipe condition, the log is affected by many factors, for instance, the pipe electrical properties and pipe geometry including number, size, and shape. Therefore, the well diagram is divided into several zones according to pipe configuration. Each zone has a consistent configuration, like pipe number and pipe size. "Zone nominals" refer to nominal pipe parameter (e.g., pipe outer diameter, thickness, eccentricity, etc) for each zone. The nominals are usually known.

At block 708B, the system constructs a monotonically piece-wise linear mapping function. A monotonically piece-wise linear mapping function defines the relationship of responses between the R1D model and the 2D model. Here, the system will construct non-linear mapping functions and map the R1D synthetic log using the non-linear mapping functions to obtain a quasi 2D log. To construct the mapping function, adjacent zones are defined as having one more or one less pipe number. For example, zone 2 in FIG. 1 consists of four pipes, and its adjacent zones 1 (one more pipe) and zone 3 (one less pipe) could be selected (the adjacent zones do not have to be physically connected).

At block 708C, if the defect is found to be below full resolution (i.e., the axial length of the defect is shorter than the length required for the defect to be accurately estimated by the tool), the system convolves the 1D log with the impulse responses to generate a quasi 2D log to include the defect 2D feature. The impulse response can be obtained by running the 2D modeling for a defect with a small amount of metal loss along both the radial and axial directions.

Meanwhile, at block 708D and 708E, the system models the zone nominals using 2-dimensional (2D) modeling and models the impulse responses, respectively. Once the zones are determined by the system, the impulse responses based on 1D model and 2D model should be used to establish the relationship between them.

Figure 8:
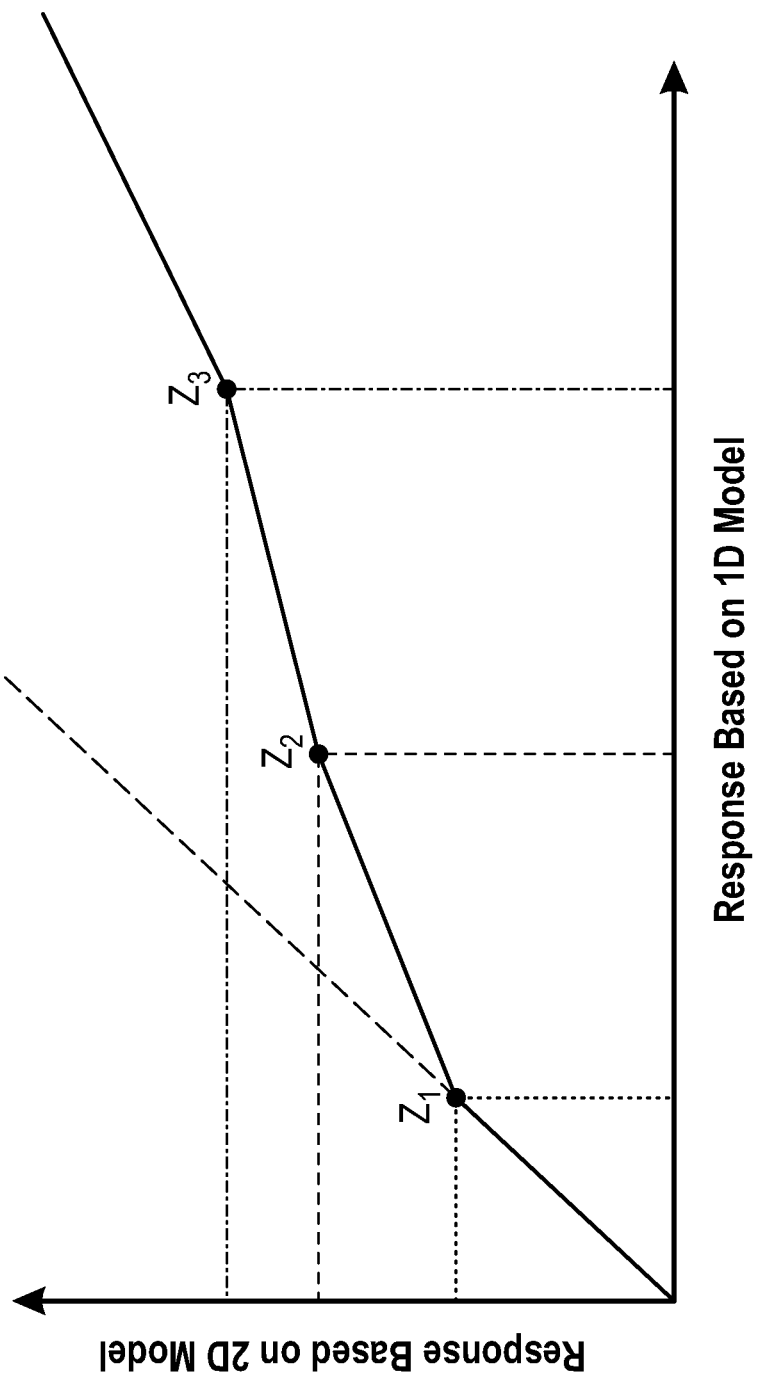
FIG. 8 is a graph showing the monotonically piece-wise linear mapping function between synthetic data based on 1D model and that based on 2D model.

FIG. 8 is a graph showing the monotonically piece-wise linear mapping function between synthetic data based on 1D model and that based on 2D model. As shown in the graph, z1, z2, and z3 are pairs of the 1D and 2D model responses for zone 1, 2, and 3 with nominal pipe parameters.

As can be seen in block 708, in order to accelerate the modeling in this example, only 121D modeling is used to generate various pipe defect scenarios (708A). Then the mapping functions are used to transfer the response based on IUD model into the 2D model domain (708B, 708D). The second step is to model the response of an impulse defect on a given pipe using 2D modeling (708E) and convolve the impulse response with the defect response (708C) from previous step to obtain quasi 2D responses at block 710. The impulse response or defect response is the measurement of the tool applied to the impulse defect being simulated. In certain illustrative embodiments, the system adds random noise to the quasi 2D log at block 708F to mimic a real environment. The noise may be introduced by adding random values within certain levels, for example within 2% of the signal level.

Alternative to generating quasi 2D logs using the method described above, a 2D electromagnetic solver can be used to model a defect scenario defined both in radial and axial dimensions to generate 2D logs. In yet another embodiment, a 3D electromagnetic solver can be used to model a defect scenario defined in radial, axial, and azimuthal dimensions to generate 3D logs. 2D and 3D logs have higher fidelity than the quasi 2D logs, but the formers require significantly higher computational resources and run time.

Once the quasi 2D logs are generated at block 710, the data is further processed at block 712 using model-based inversion to obtain estimates of modeled pipe parameters (e.g., pipe thicknesses) at block 714. At block 716, the system then analyzes the accuracy, resolution, and stability of inversion results by comparing them to the true pipe profile contains defect information in order to determine the tool's performance. At block 718, the system then analyzes the estimates of modeled pipe parameters to obtain performance metrics (resolution metrics). At block 720, the system generates and outputs recommendations and/or adjustments (optimizations) to the inspection tools, as described herein, such as for example, to the logging speed, array selection and power levels. Thereafter, the an existing tool may be adjusted or a modular tool may be assembled to incorporate the optimizations, deployed into a well and operated as described herein.

Figure 9:
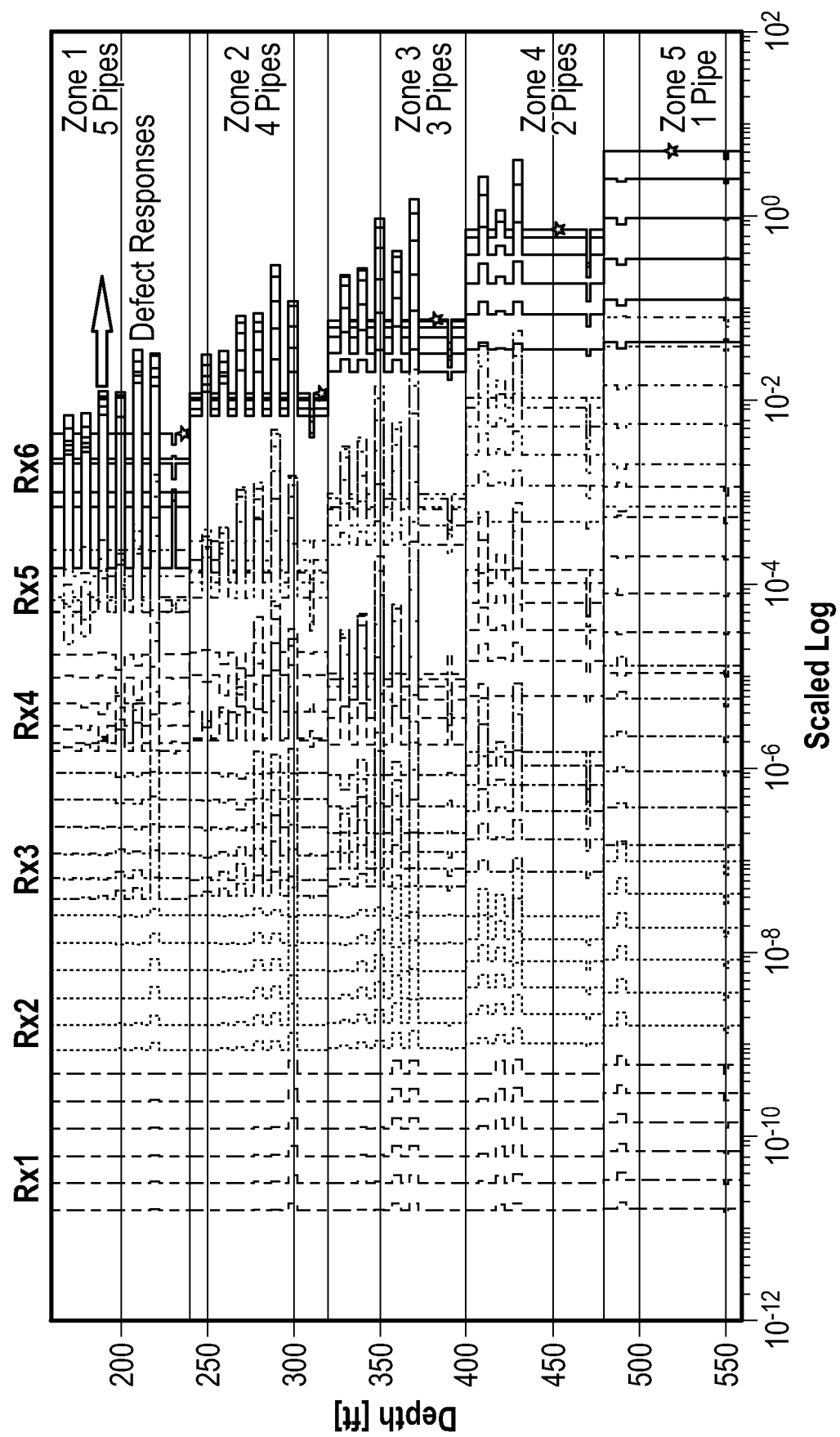
FIG. 9 show an example of a quasi 2D log, corresponding to block 710 of method workflow 700.

FIG. 9 show an example of the quasi 2D log, corresponding to block 710. The log corresponds to a well with five pipes of different lengths. The nominal responses for each zone are indicated by stars (from block 708D). All squared-shape indicators are defect responses. The defect responses are from block 708B.

Figure 10:
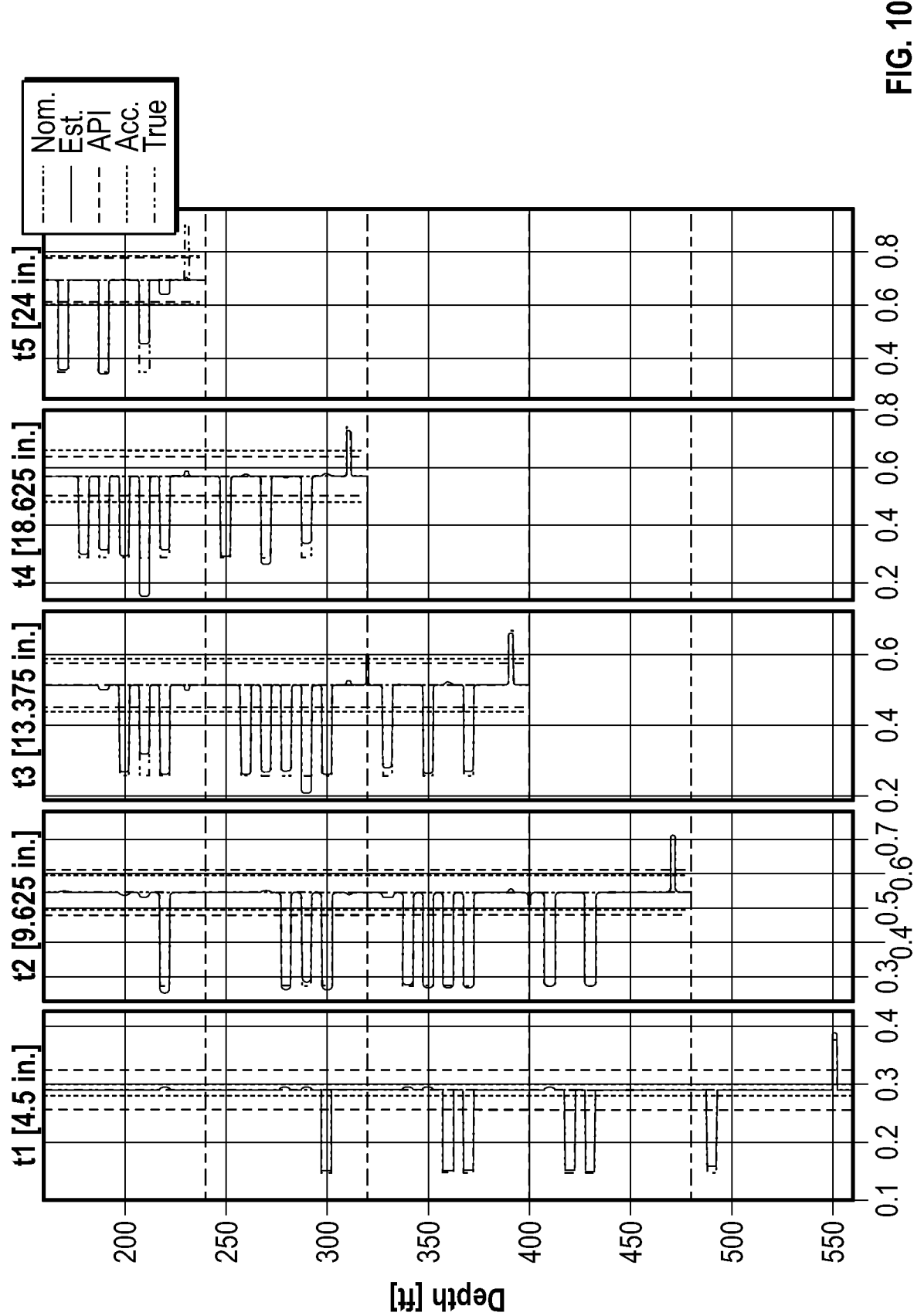
FIG. 10 is a graph of the inversion results of the log in FIG. 9.

FIG. 10 is a graph of the inversion results of the log in FIG. 9. The rectangular blocks are inverted individual pipe thicknesses. True pipe thickness are also shown. Comparing the inverted and true pipe thickness and using statistics analysis, the system of the present disclosure determines the tool accuracy and vertical resolution.

Figure 11:
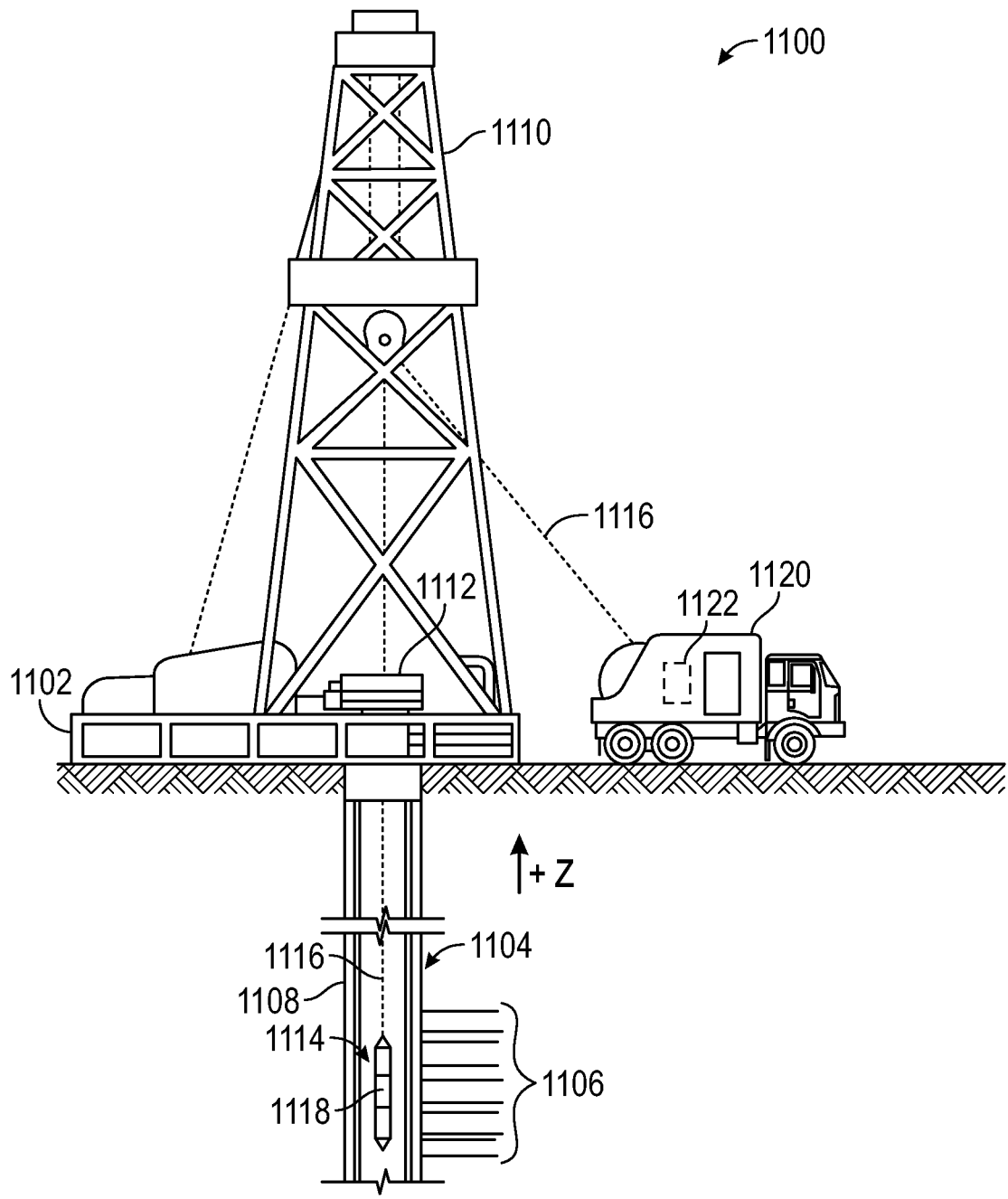
FIG. 11 illustrates an exemplary diagrammatic view of a conveyance logging wellbore operating environment in which the present disclosure may be implemented.

FIG. 11 illustrates a diagrammatic view of a conveyance logging wellbore operating environment 1100 (also referred to as "wireline" in the field) in which the present disclosure may be implemented. As depicted in FIG. 11, the wireline system 1100 may include a surface platform 1102 positioned at the Earth's surface and a wellbore 1104 that extends from the surface platform 1102 into one or more subterranean formations 1106. In other embodiments, such as in offshore operations, a volume of water may separate the surface platform 1102 and the wellbore 1104. The wellbore 1104 may be lined with one or more pipes 1108, also referred to as strings of casing. In some embodiments, portions of the wellbore 1104 may have only one pipe 1108 positioned therein, but other portions of the wellbore 1104 may be lined with two or more concentrically disposed pipes 1108. The pipes 1108 may be made of plain carbon steel, stainless steel, or another material capable of withstanding a variety of forces, such as collapse, burst, and tensile failure.

The wireline system 1100 may include a derrick 1110 supported by the surface platform 1102 and a wellhead installation 1112 positioned at the top of the wellbore 1104. A pipe inspection tool 1114, according to any of the illustrative embodiments described herein, may be suspended into the wellbore 1104 on a cable 1116. In some embodiments, the pipe inspection tool 1114 may alternatively be suspended within production tubing or pipe (not shown) positioned within the pipes 1108 that line the wellbore 1104 (i.e., casing). In such embodiments, the production tubing may extend by itself into the pipes 1108 or alternatively be positioned adjacent one or more eccentrically located production pipes that are also positioned within the pipes 1108. Accordingly, the pipes 1108 may refer to strings of casing lining the wellbore 1104 or at least one production pipe extended within casing that lines the wellbore 1104.

The pipe inspection tool 1114 may be any of the illustrative inspection tools described herein. For example, the pipe inspection tool 1114 may comprise one of a frequency-domain Eddy current tool or a time-domain Eddy current tool. Accordingly, its operation may be based on either the flux-leakage principle or the eddy-current principle, or a combination of both. Moreover, the pipe inspection tool 1114 may be insensitive to non-conductive deposits and is operable irrespective of the nature of the fluid mixture flowing into/out of the wellbore 1104. The pipe inspection tool 1114 can be used for the detection of various features associated with the pipes 1108, such as, but not limited to, a pipe collar, a metal gain region, a metal loss region, a deformed region, one or more perforations defined in the pipes 1108, localized damage, a defect, and corrosion in the pipes 1108. Such features can either be man-made or caused by corrosion.

In operation, the pipe inspection tool 1114 subjects the pipes 1108 to a strong static magnetic field using one or more transmitters and, due to the ferromagnetic nature of the pipes 1108, the magnetic return flux is mainly confined to the inside of the pipes 1108. In the presence of discontinuities or defects in the metal, such as any of the features listed above, changes in the magnetic field can be detected with one or more electromagnetic sensors 1118 included in the pipe inspection tool 1114.

The electromagnetic sensors 1118 may be communicably coupled to the cable 1116, which may include conductors for conveying power to the pipe inspection tool 1114 and also for facilitating communication between the surface platform 1102 and the pipe inspection tool 1114. A logging facility 1120, shown in FIG. 10 as a truck, may collect measurements obtained by the electromagnetic sensors 1118, and may include computing devices 1122 for controlling, processing, storing, and/or visualizing the measurements gathered by the electromagnetic sensors 1118. The computing devices 1122 may be communicably coupled to the pipe inspection tool 1114 by way of the cable 1116. The computing devices 1122 is capable of carrying out the methods and techniques of the present disclosure.

The electromagnetic sensors 1118 may include one or more electromagnetic coil antennas that may be used as transmitters, receivers, or a combination of both (i.e., transceivers) for obtaining in situ measurements of the pipe(s) 1108. In some embodiments, the electromagnetic sensors 1118 may be designed to operate in a centralized position within the innermost pipe 1108, such as through the use of one or more centralizers (not shown) attached to the body of the pipe inspection tool 1114. In other embodiments, however, the electromagnetic sensors 1118 may be designed to be adjacent or in intimate contact with the inner wall of the innermost pipe 1108. In such embodiments, the electromagnetic sensors 1118 may be mounted on one or more deployable sensor pads (not shown) positioned on actuatable arms that move the electromagnetic sensors 1118 radially outward toward the inner wall of the innermost pipe 1108.

Figure 12:
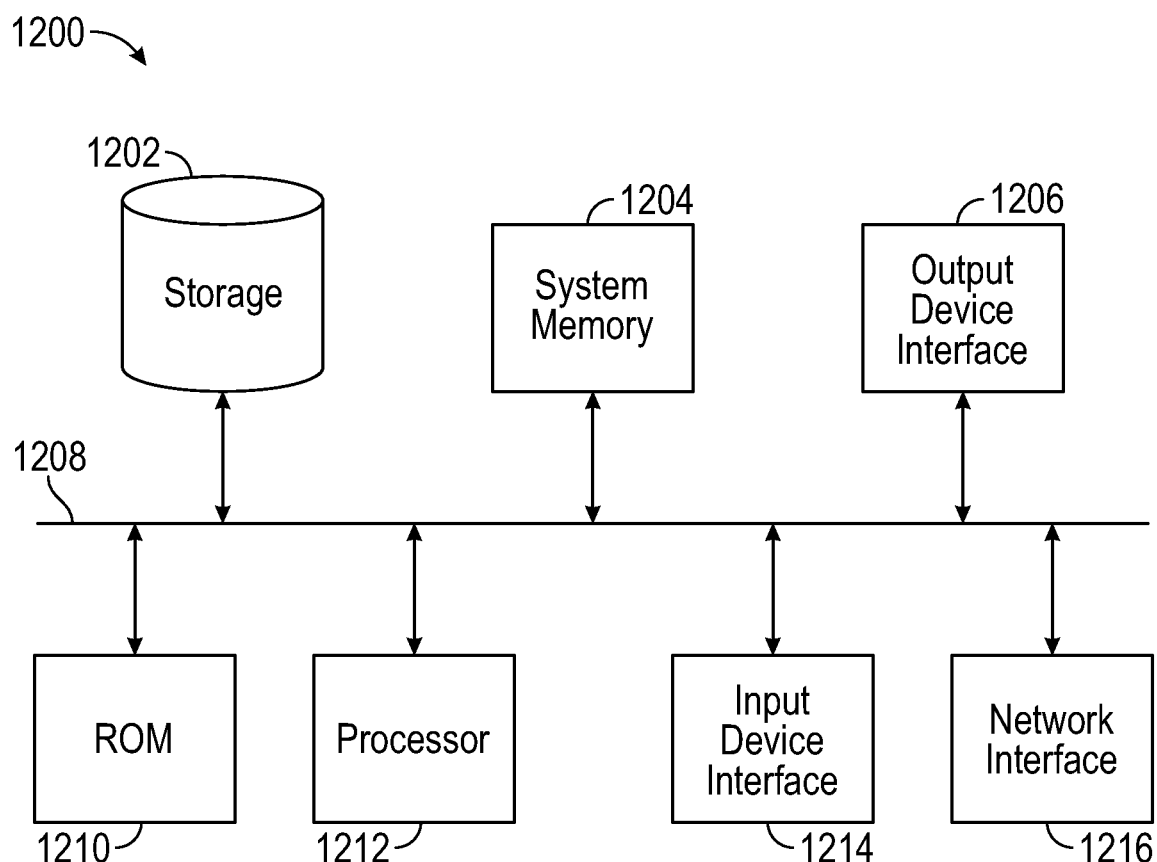
FIG. 12 is a block diagram of an exemplary computer system in which embodiments of the present disclosure may be implemented.

FIG. 12 is a block diagram of an exemplary computer/control system 1200 in which embodiments of the present disclosure may be implemented. System 1200 can be a computer, phone, PDA, or any other type of electronic device. Such an electronic device includes various types of computer readable media and interfaces for various other types of computer readable media. As shown in FIG. 12, system 1200 includes a permanent storage device 1202, a system memory 1204, an output device interface 1206, a system communications bus 1208, a read-only memory (ROM) 1210, processing unit(s) 1212, an input device interface 1214, and a network interface 1216.

Bus 1208 collectively represents all system, peripheral, and chipset buses that communicatively connect the numerous internal devices of system 1200. For instance, bus 1208 communicatively connects processing unit(s) 1212 with ROM 1210, system memory 1204, and permanent storage device 1202.

From these various memory units, processing unit(s) 1212 retrieves instructions to execute and data to process in order to execute the processes of the subject disclosure. The processing unit(s) can be a single processor or a multi-core processor in different implementations.

ROM 1210 stores static data and instructions that are needed by processing unit(s) 1212 and other modules of system 1200. Permanent storage device 1202, on the other hand, is a read-and-write memory device. This device is a non-volatile memory unit that stores instructions and data even when system 1200 is off. Some implementations of the subject disclosure use a mass-storage device (such as a magnetic or optical disk and its corresponding disk drive) as permanent storage device 1202.

Other implementations use a removable storage device (such as a floppy disk, flash drive, and its corresponding disk drive) as permanent storage device 1202. Like permanent storage device 1202, system memory 1204 is a read-and-write memory device. However, unlike storage device 1202, system memory 1204 is a volatile read-and-write memory, such a random access memory. System memory 1204 stores some of the instructions and data that the processor needs at runtime. In some implementations, the processes of the subject disclosure are stored in system memory 1204, permanent storage device 1202, and/or ROM 610. For example, the various memory units include instructions for computer aided pipe string design based on existing string designs in accordance with some implementations. From these various memory units, processing unit(s) 1212 retrieves instructions to execute and data to process in order to execute the processes of some implementations.

Bus 1208 also connects to input and output device interfaces 1214 and 1206. Input device interface 1214 enables the user to communicate information and select commands to the system 1200. Input devices used with input device interface 1214 include, for example, alphanumeric, QWERTY, or T9 keyboards, microphones, and pointing devices (also called "cursor control devices"). Output device interfaces 1206 enables, for example, the display of images generated by the system 1200. Output devices used with output device interface 1206 include, for example, printers and display devices, such as cathode ray tubes (CRT) or liquid crystal displays (LCD). Some implementations include devices such as a touchscreen that functions as both input and output devices. It should be appreciated that embodiments of the present disclosure may be implemented using a computer including any of various types of input and output devices for enabling interaction with a user. Such interaction may include feedback to or from the user in different forms of sensory feedback including, but not limited to, visual feedback, auditory feedback, or tactile feedback. Further, input from the user can be received in any form including, but not limited to, acoustic, speech, or tactile input. Additionally, interaction with the user may include transmitting and receiving different types of information, e.g., in the form of documents, to and from the user via the above-described interfaces.

Also, as shown in FIG. 12, bus 1208 also couples system 1200 to a public or private network (not shown) or combination of networks through a network interface 1216. Such a network may include, for example, a local area network ("LAN"), such as an Intranet, or a wide area network ("WAN"), such as the Internet. Any or all components of system 1200 can be used in conjunction with the subject disclosure.

These functions described above can be implemented in digital electronic circuitry, in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself. Accordingly, the steps of processes described above may be implemented using system 600 or any computer system having processing circuitry or a computer program product including instructions stored therein, which, when executed by at least one processor, causes the processor to perform functions relating to these methods.

As used in this specification and any claims of this application, the terms "computer", "server", "processor", and "memory" all refer to electronic or other technological devices. These terms exclude people or groups of people. As used herein, the terms "computer readable medium" and "computer readable media" refer generally to tangible, physical, and non-transitory electronic storage mediums that store information in a form that is readable by a computer.

The computing system can include clients and servers. A client and server are generally remote from each other and typically interact through a communication network. The relationship of client and server arises by virtue of computer programs running on the respective computers and having a client-server relationship to each other. In some embodiments, a server transmits data (e.g., a web page) to a client device (e.g., for purposes of displaying data to and receiving user input from a user interacting with the client device). Data generated at the client device (e.g., a result of the user interaction) can be received from the client device at the server.

It is understood that any specific order or hierarchy of steps in the processes disclosed is an illustration of exemplary approaches. Based upon design preferences, it is understood that the specific order or hierarchy of steps in the processes may be rearranged, or that all illustrated steps be performed. Some of the steps may be performed simultaneously. For example, in certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

In view of the foregoing, the optimized inspection tools and methods disclosed herein will provide efficient methods to generate synthetic logs that are used for model-based inversion. Based on the estimated pipe parameters, the tool performance metrics can be studied. Further, the illustrative embodiments provide reconfigurable electromagnetic pipe inspection tools which can be adjusted based on the well diagram to obtain best performance for each individual well.

The disclosed embodiments and methods provide several advantages. The proposed methods provide precise tool specifications, optimal tool configuration for field engineer to plan jobs and determine logging speeds for each particular well. The embodiments and methods can also reduce operation time and cost for downhole operations. The tool performance metrics estimation (e.g., accuracy, sensitivity, and resolution) will also aid analysts as field logs are processed.

Embodiments and methods of the present disclosure described herein further relate to any one or more of the following paragraphs:

1. A method for inspecting nested wellbore pipes using an electromagnetic pipe inspection tool, the method comprising obtaining well plan information; modeling, based on the well plan information, a pipe inspection tool in a pipe inspection scenario to obtain synthetic data; analyzing the synthetic data to obtain performance metrics of the pipe inspection tool using a set of tool parameters; adjusting the tool parameters to optimize the performance metrics of the pipe inspection tool; acquiring measured data from a physical pipe inspection tool, positioned in a well, having the adjusted tool parameters; and processing the measured data to obtain estimates of well pipe parameters.
2. The method as defined in paragraph 1, wherein modeling the pipe inspection scenario comprises modeling pipe parameters with at least one defect in at least one pipe.
3. The method as defined in paragraphs 1 or 2, wherein the performance metrics include one of a sensitivity, signal-to-noise ratio, or vertical resolution of the pipe inspection tool.
4. The method as defined in any of paragraphs 1-3, wherein the modeling is performed using a radial 1-dimensional electromagnetics model, a 2-dimensional model or a 3-dimensional model.
5. The method as defined in any of paragraphs 1-4, wherein analyzing the synthetic data comprises processing the synthetic data using model-based inversion to obtain estimates of modeled pipe parameters; and adjusting the tool parameters comprises adjusting the tool parameters to optimize performance metrics based on the estimates of modeled pipe parameters.
6. The method as defined in any of paragraphs 1-5, wherein the performance metrics are determined based upon inversion accuracy in resolving individual pipe thickness, inversion vertical resolution, or inversion stability.
7. The method as defined in any of paragraphs 1-6, wherein modeling the pipe inspection tool comprises modeling the pipe inspection tool using a radial 1-dimensional (R1D) computer model to obtain the R1D synthetic data; modeling zone nominals using 2-dimensional (2D) modeling; constructing one or more non-linear mapping functions; mapping the R1D synthetic data using the non-linear mapping functions to obtain a quasi 2D log; and analyzing the synthetic data to obtain performance metrics comprises: processing the quasi 2D log through inversion to obtain estimates of the modeled pipe parameters; and analyzing the estimates of the modeled pipe parameters to obtain the performance metrics.
8. The method as defined in any of paragraphs 1-7, further comprising modeling a response of an impulse defect on a given pipe using 2D modeling; and convolving the response of the impulse defect with a defect response modeled using R1D modeling to obtain quasi 2D responses of defects below a vertical resolution of the inspection tool.
9. The method as defined in any of paragraphs 1-8, further comprising adding random noise to the quasi 2D log; applying inversion to the noisy quasi 2D log; and analyzing an accuracy and stability of inversion results to random noise realizations in order to calculate tool metrics and thereby evaluate tool performance.
10. The method in any of paragraphs 1-9, wherein adjusting the tool parameters comprises adjusting one of an excitation current power, excitation current frequency, excitation pulse duration, excitation pule slew rate, decay response recording time duration, decay response sampling rate, or logging speed.
11. A system for inspecting nested wellbore pipes using an electromagnetic pipe inspection tool, the system comprising processing circuitry to perform operations comprising obtaining well plan information; modeling, based on the well plan information, a pipe inspection tool in a pipe inspection scenario to obtain synthetic data; analyzing the synthetic data to obtain performance metrics of the pipe inspection tool using a set of tool parameters; adjusting the tool parameters to optimize the performance metrics of the pipe inspection tool; acquiring measured data from a physical pipe inspection tool, positioned in a well, with the adjusted tool parameters; and processing the measured data to obtain estimates of well pipe parameters.

Furthermore, the exemplary methodologies described herein may be implemented by a system including processing circuitry or a non-transitory computer program product including instructions which, when executed by at least one processor, causes the processor to perform any of the methodology described herein.

Although various embodiments and methodologies have been shown and described, the invention is not limited to such embodiments and methodologies and will be understood to include all modifications and variations as would be apparent to one skilled in the art. Therefore, it should be understood that the invention is not intended to be limited to the particular forms disclosed. Rather, the intention is to cover all modifications, equivalents and alternatives falling within the spirit and scope of the invention as defined by the appended claims.

What is claimed is:

1. A method for inspecting nested wellbore pipes using an electromagnetic pipe inspection tool, the method comprising:
    customizing the electromagnetic pipe inspection tool prior to running the electromagnetic pipe inspection tool in hole by:
        obtaining a well plan information, wherein the well plan information comprises information on at least one of a nominal outer diameter of the nested wellbore pipes, a nominal thickness of each one of the nested wellbore pipes, a start and an end depth of each one of the nested wellbore pipes, a grade and a weight of each one of the nested wellbore pipes, and a type of metal of each one of the nested wellbore pipes;
        modeling, based on the well plan information, the electromagnetic pipe inspection tool in a pipe inspection scenario to obtain synthetic data using at least one of two-dimensional (2D) forward model and a radial one-dimensional (R1D) electromagnetic forward model;
        analyzing the synthetic data using a model-based inversion to obtain estimates of performance metrics of the pipe inspection tool for a set of tool parameters comprising an array of transmitters and receivers, an axial distance between each transmitter and receiver, exciting pre-determined transmitters and acquiring data from pre-determined receivers;

adjusting the tool parameters to optimize the performance metrics of the pipe inspection tool;
disposing of the electromagnetic pipe inspection tool in a wellbore;
acquiring measured data from the electromagnetic pipe inspection tool positioned in the wellbore having the adjusted tool parameters; and
processing the measured data to obtain estimates of well pipe parameters using the model-based inversion.

2. The method as defined in claim 1, wherein modeling the pipe inspection scenario comprises modeling pipe parameters with at least one defect in at least one pipe.

3. The method as defined in claim 1, wherein the performance metrics include one of a sensitivity, signal-to-noise ratio, or vertical resolution of the pipe inspection tool.

4. The method as defined in claim 1, wherein the modeling is performed using a radial 1-dimensional electromagnetics model, a 2-dimensional model or a 3-dimensional model.

5. The method as defined in claim 1, wherein:
analyzing the synthetic data comprises processing the synthetic data using model-based inversion to obtain estimates of modeled pipe parameters; and
adjusting the tool parameters comprises adjusting the tool parameters to optimize performance metrics based on the estimates of modeled pipe parameters.

6. The method as defined in claim 5, wherein the performance metrics are determined based upon inversion accuracy in resolving individual pipe thickness, inversion vertical resolution, or inversion stability.

7. The method as defined in claim 1, wherein:
modeling the pipe inspection tool comprises:
modeling the pipe inspection tool using a radial 1-dimensional (R1D) computer model to obtain the R1D synthetic data;
modeling zone nominals using 2-dimensional (2D) modeling;
constructing one or more non-linear mapping functions;
mapping the R1D synthetic data using the non-linear mapping functions to obtain a quasi 2D log; and
analyzing the synthetic data to obtain performance metrics comprises:
processing the quasi 2D log through inversion to obtain estimates of the modeled pipe parameters; and
analyzing the estimates of the modeled pipe parameters to obtain the performance metrics.

8. The method as defined in claim 7, further comprising:
modeling a response of an impulse defect on a given pipe using 2D modeling; and
convolving the response of the impulse defect with a defect response modeled using R1D modeling to obtain quasi 2D responses of defects below a vertical resolution of the inspection tool.

9. The method as defined in claim 7, further comprising:
adding random noise to the quasi 2D log;
applying inversion to the noisy quasi 2D log; and
analyzing an accuracy and stability of inversion results to random noise realizations in order to calculate tool metrics and thereby evaluate tool performance.

10. The method in claim 1, wherein adjusting the tool parameters comprises adjusting one of an excitation current power, excitation current frequency, excitation pulse duration, excitation pule slew rate, decay response recording time duration, decay response sampling rate, or logging speed.

11. A non-transitory computer memory including instructions which, when executed by at least one processor, causes the processor to perform a method comprising:
customizing a pipe inspection tool prior to running the pipe inspection tool in hole by;
obtaining well plan information, wherein the well plan information comprises information on at least one a nominal outer diameter of a nested wellbore pipes, a nominal thickness of each one of the nested wellbore pipes, a start and an end depth of each one of the nested wellbore pipes, a grade and a weight of each one of the nested wellbore pipes, and a type of metal of each one of the nested wellbore pipes:
modeling, based on the well plan information, the pipe inspection tool in a pipe inspection scenario to obtain synthetic data using at least one of two-dimensional (2D) electromagnetic forward modeling and a radial one-dimensional (R1D) electromagnetic forward model;
analyzing the synthetic data using a model-based inversion to obtain estimates of performance metrics of the pipe inspection tool using a set of tool parameters comprising an array of transmitters and receivers, an axial distance between each transmitter and receiver, exciting pre-determined transmitters and acquiring data from pre-determined receivers;
adjusting the tool parameters to optimize the performance metrics of the pipe inspection tool;
disposing of the electromagnetic pipe inspection tool in a wellbore
acquiring measured data from a physical pipe inspection tool, positioned in the wellbore, having the adjusted tool parameters; and
processing the measured data to obtain estimates of well pipe parameters using the model-based inversion.

12. The non-transitory computer memory as defined in claim 11, wherein:
modeling the pipe inspection scenario comprises modeling pipe parameters with at least one defect in at least one pipe; or
the modeling is performed using a radial 1-dimensional electromagnetics model, a 2-dimensional model or a 3-dimensional model.

13. The non-transitory computer memory as defined in claim 11, wherein the performance metrics include one of a sensitivity, signal-to-noise ratio, or vertical resolution of the pipe inspection tool.

14. The non-transitory computer memory as defined in claim 11, wherein:
analyzing the synthetic data comprises processing the synthetic data using model-based inversion to obtain estimates of modeled pipe parameters; and
adjusting the tool parameters comprises adjusting the tool parameters to optimize performance metrics based on the estimates of modeled pipe parameters.

15. The non-transitory computer memory as defined in claim 14, wherein the performance metrics are determined based upon inversion accuracy in resolving individual pipe thickness, inversion vertical resolution, or inversion stability.

16. The non-transitory computer memory as defined in claim 11, wherein:
modeling the pipe inspection tool comprises:
modeling the pipe inspection tool using a radial 1-dimensional (R1D) computer model to obtain the R1D synthetic data;

modeling zone nominals using 2-dimensional (2D) modeling;

constructing one or more non-linear mapping functions; and mapping the R1D synthetic data using the non-linear mapping functions to obtain a quasi 2D log; and analyzing the synthetic data to obtain performance metrics comprises:

processing the quasi 2D log through inversion to obtain estimates of the modeled pipe parameters; and analyzing the estimates of the modeled pipe parameters to obtain the performance metrics.

17. The non-transitory computer memory as defined in claim 16, further comprising:

modeling a response of an impulse defect on a given pipe using 2D modeling; and convolving the response of the impulse defect with a defect response modeled using R1D modeling to obtain quasi 2D responses of defects below a vertical resolution of the inspection too.

18. The non-transitory computer memory as defined in claim 16, further comprising:

adding random noise to the quasi 2D log;

applying inversion to the noisy quasi 2D log; and analyzing an accuracy and stability of inversion results to random noise realizations in order to calculate tool metrics and thereby evaluate tool performance.

19. The non-transitory computer memory as defined in claim 11, wherein adjusting the tool parameters comprises adjusting one of an excitation current power, excitation current frequency, excitation pulse duration, excitation pule slew rate, decay response recording time duration, decay response sampling rate, or logging speed.

20. A system for inspecting nested wellbore pipes using an electromagnetic pipe inspection tool, the system comprising processing circuitry to perform operations comprising:

customizing the electromagnetic pipe inspection tool prior to running the electromagnetic pipe inspection tool in hole by:

obtaining a well plan information, wherein the well plan information comprises information on at least one of a nominal outer diameter of the nested wellbore pipes, a nominal thickness of each one of the nested wellbore pipes, a start and an end depth of each one of the nested wellbore pipes, a grade and a weight of each one of the nested wellbore pipes, and a type of metal of each one of the nested wellbore pipes;

modeling, based on the well plan information, the electromagnetic pipe inspection tool in a pipe inspection scenario to obtain synthetic data using at least one of two-dimensional (2D) electromagnetic forward model and a radial one-dimensional (R1D) electromagnetic model;

analyzing the synthetic data using model-based inversion to obtain estimates of performance metrics of the electromagnetic pipe inspection tool using a set of tool parameters comprising an array of transmitters and receivers, an axial distance between each transmitter and receiver, exciting pre-determined transmitters, and acquiring data from pre-determined receivers;

adjusting the tool parameters to optimize the performance metrics of the pipe inspection tool;

acquiring measured data from the electromagnetic pipe inspection tool, positioned in a wellbore, with the adjusted tool parameters; and processing the measured data to obtain estimates of well pipe parameters using the model-based inversion.

* * * * *